United States Patent
Carr, Jr. et al.

(10) Patent No.: US 7,192,726 B1
(45) Date of Patent: Mar. 20, 2007

(54) METHOD OF USING PLATELET CONTRACTILE FORCE AND WHOLE BLOOD CLOT ELASTIC MODULUS AS CLINICAL MARKERS

(75) Inventors: Marcus E. Carr, Jr., Midlothian, VA (US); Ashok Krischnaswami, San Jose, CA (US); Erika Martin, Richmond, VA (US)

(73) Assignee: Hemodyne, Inc., Bethesda, MD (US)

( * ) Notice: Subject to any disclaimer, the term of this patent is extended or adjusted under 35 U.S.C. 154(b) by 653 days.

(21) Appl. No.: 10/049,374

(22) PCT Filed: Aug. 11, 2000

(86) PCT No.: PCT/US00/21848

§ 371 (c)(1),
(2), (4) Date: Apr. 17, 2002

(87) PCT Pub. No.: WO01/12211

PCT Pub. Date: Feb. 22, 2001

Related U.S. Application Data

(60) Provisional application No. 60/148,595, filed on Aug. 13, 1999.

(51) Int. Cl.
*C12Q 1/56* (2006.01)

(52) U.S. Cl. ........................................................ 435/13

(58) Field of Classification Search .................. 435/13, 435/4, 2
See application file for complete search history.

(56) References Cited

U.S. PATENT DOCUMENTS

| | | | | |
|---|---|---|---|---|
| 4,986,964 A | * | 1/1991 | Carr et al. | 422/73 |
| 5,106,186 A | * | 4/1992 | Carr, Jr. | 356/39 |
| 5,118,182 A | * | 6/1992 | Carr, Jr. | 356/39 |
| 5,205,159 A | * | 4/1993 | Carr, Jr. | 73/64.41 |
| 5,293,772 A | * | 3/1994 | Carr, Jr. | 73/64.41 |
| 2002/0068719 A1 | * | 6/2002 | Wong et al. | 514/56 |

OTHER PUBLICATIONS

Ramsis, Nevene et al, Pathophysiology of Haemostasis and Thrombosis, vol. 28, No. 5, Abstract on pp. 1-2, (1998).*
Greilich P. et al. Quantitative Assessment of Platelet Function and Clot Structure in Patients with Severe CAD. The American J of the Medical Scineces 307(1)15-20, 1994.*

* cited by examiner

*Primary Examiner*—Ralph Gitomer
(74) *Attorney, Agent, or Firm*—Whitham, Curtis, Christofferson & Cook PC

(57) ABSTRACT

Platelet contractile force and/or clot elastic modulus measurements are used to identify patients at risk for atherosclerosis or for bleeding during surgical procedures or other applications. Measurements which are elevated are indicative of atherosclerosis, and measurements which are reduced are indicative of a bleeding risk.

6 Claims, 9 Drawing Sheets

US 7,192,726 B1

METHOD OF USING PLATELET CONTRACTILE FORCE AND WHOLE BLOOD CLOT ELASTIC MODULUS AS CLINICAL MARKERS

This application is a National Stage Application filed under Rule 371 based upon PCT/US00/21848 filed Aug. 11, 2000 which claims benefit of 60/148,595 filed Aug. 13, 1999.

BACKGROUND OF THE INVENTION

1. Field of the Invention

The invention is related to a method which uses platelet contractile force (PCF) measurements and/or clot elastic modulus (CEM) as clinical markers to allow rapid assessment of a patient's risk of atherosclerosis or a patient's bleeding risk during surgical procedures.

2. Description of the Prior Art

The interplay between atherosclerosis and thrombosis is complex. Multiple local and systemic thrombotic risk factors have been shown to play a role in the destabilization of the vulnerable plaque and its clinical sequelae. Aside from local factors such as the degree of plaque erosion or stenosis, well known systemic risk factors include cholesterol, diabetes mellitus, tobacco, cocaine, hypertension, elevated fibrinogen, impaired fibrinolysis, activated platelets and products or by-products of the coagulation cascade.

Platelet activation occurs in the acute coronary syndrome[1]. The acute coronary syndrome is a continuum from unstable angina to non-Q and Q-wave myocardial infarction depending on the extent and duration of ischemia. Reduction in coronary blood flow occurs due to platelet aggregation, vasoconstriction at the site of coronary artery stenosis and endothelial injury. Endothelial injury may result from plaque ulceration, hemodynamic factors, systemic arterial hypertension, cardiac catherization, balloon angioplasty, etc. [2,3,4,5]. It is critical to recognize the acute coronary syndrome in patients who present to an emergency department with chest pain in order to prevent inappropriate discharge and adverse consequences[6,7].

Sensitive assays of individual components of the coagulation cascade have made laboratory evaluation of a biochemical hypercoagulable state possible. Prospective studies have suggested that elevated levels of factor VII, fibrinogen and other markers are associated with the development of ischemic cardiac events. However, traditional risk factors have not explained the increased cardiovascular risk in certain high risk groups such as diabetics. The contribution of platelet activation in patients presenting with an acute coronary syndrome has been well established. Unfortunately, to this point, tests of platelet function have not reflected changes predictive of a hypercoagulable state.

Platelet aggregometry, nuclear imaging techniques, serum markers such as Troponin I and T, P-selectin and E-selectin, intercellular adhesion molecules (ICAM) are some of the tools currently available and under investigation to identify patients with acute cardiac events. Nuclear imaging with technetium-99m sestamibi requires considerable resource utilization and has limited ability to differentiate between ischemia, ongoing infarction and prior infarction. Technetium-99m sestamibi also does not identify the unstable plaque [8,9,10]. Elevations of troponin in patients who have myocardial infarction excluded predict an increased risk for short and long term adverse cardiac events. Their utility in acute events is limited since some degree of myocardial necrosis must occur prior to their release [11]. Platelet aggregation may be a useful marker for predicting mortality in coronary events [12]. However, aggregation techniques that have been used to evaluate platelet dysfunction have been limited to a few non-cardiac clinical situations [13]. Measurement of P-selectin [13], ICAM-1 and/or E-selectin [14] as early markers of platelet activation is ill suited to an emergency department setting because the techniques of flow cytometry and ELISA are time consuming, require technical expertise and need substantial dedicated equipment. Newer methods to assess platelet function are needed.

The Hemodyne® Hemostasis Analyzer is an instrument which measures platelet activity (platelet contractile force, PCF) and clot strength (clot elastic modulus, CEM) in physical units of dynes & dynes/cm$^2$ respectively[15,16]. U.S. Patents on which the Hemodyne® Hemostasis Analyzer is based include U.S. Pat. No. 4,986,964, U.S. Pat. No. 5,205,159, and U.S. Pat. No. 5,293,772, and each of these patents are incorporated by reference in their entirety. FIG. 1 schematically illustrates the components of a system similar to that described in these patents, and which is employed in the Hemodyne® Hemostasis Analyzer. A blood sample obtained from a patient is deposited in a sample cup 10 using a syringe 12 or other suitable device. The cup 10 is placed in a base 14, and a head piece 16 is inserted into the cup 10. This causes the blood 18 to distribute itself along the surface of the head piece 16 and up the sides of the cup 10. The force developed during contraction pulls the head piece 16 and base 14 closer together, and this force is measured using sensors connected to either or both the head piece 16 or base 14. To avoid adverse effects of the three dimensional structure on the clot during formation, a force can be periodically applied to the blood 18 during clotting by the head piece 16.

PCF and CEM are potentially useful tools in a variety of clinical situations[17,18,19]. PCF depends on thrombin production, platelet count, platelet viability and the degree of platelet inhibition[15,20,21]. CEM depends on the fibrinogen concentration, fibrin structure and platelet function[15]. Inhibition of fibrin(ogen) binding to GP IIb/IIIa blockade either by disruption of GP IIb/IIIa or by competitive blockade, inhibits platelet mediated force development and results in clot structures which are substantially less resistant to deformation by outside forces[22].

Currently, a patient is screened for the presence of atherosclerosis by the patient's response to treadmill exercises and/or by cardiac catheterization. Both tests are time consuming and expensive, and catheterization is quite invasive to the patient. It would be helpful to have available a rapid, less invasive test which may identify those at risk for the presence of atherorsclerosis with the associated increased risk of adverse events such as myocardial infarction, peripheral vascular events, and stroke.

SUMMARY OF THE INVENTION

It is an object of this invention to provide a method which utilizes rapid recognition and quantification of platelet activation in patients to identify those at risk for adverse vascular events including thrombosis and hemorrhage.

There have been indications that PCF maybe elevated in patients with known coronary artery disease (CAD) when compared to normal control[23], and that CEM is elevated in CAD patients and is reduced, but not normalized, by aspirin therapy (FIGS. 2 and 3 show data illustrating these phenomena). Thus, it is widely acknowledged that platelets play a major role in arterial thrombosis and are thought to be pivotal in the pathogenesis of atherosclerosis. Despite these acknowledged relationships, no laboratory parameter has been demonstrated to be of value in the determination of thrombotic tendency due to platelet activity. Platelet count, the most commonly measured platelet parameter, does not correlate with thrombotic risk. It is well known that high platelet counts do not imply an increased risk of thrombosis. Other common tests of platelet functions such as the bleeding time and platelet aggregation studies do not correlate with bleeding or thrombotic risk.

This invention provides a methodology where PCF and CEM are used to rapidly assess the risk of a patient for thrombotic events associated with atherosclerosis or with the risk of bleeding associated with deficient platelet function. Prior studies have not demonstrated that these measures could be used effectively as a screen for probable patient risk. In this invention, it is demonstrated that there is a statistically relevant correlation between PCF and/or CEM and thrombotic risk in patients with atherosclerosis. It is also demonstrated that there is a statistically relevant correlation between PCF and/or CEM and a patient's bleeding risk.

In the emergency department, the measurement of PCF and CEM could be used to detect evidence of hyper-platelet function associated with atherosclerosis in patients presenting with chest pain. Since the presence of atherosclerosis is the greatest risk factor for having a myocardial infarction, this piece of clinical evidence could be used to triage patients toward admission to the hospital or discharge to home. If the force is low or normal, the patient is less likely to have atherosclerosis and is therefore at lower risk of having a myocardial infarction. If the force is elevated two standard deviations above normal, the patient is at high risk even if the clinical history is not compelling.

While PCF and CEM will not diagnosis myocardiaol infarction, they do help identify the most important risk factor and therefore aid in the decision to admit and treat. This is a time consuming and expensive process in the emergency department. Despite the expense and effort, patients are sent home from emergency rooms every day in the United States who are having a myocardial infarction. Some of these patients die of their event. Conversely, millions are spent admitting and monitoring patients who are not having a mycardial infarction.

Virtually all therapies used in the acute treatment of unstable angina and myocardial infarction result in a decline in PCF and CEM. Heparin anticoagulation, blockade of the platelet receptor glycoprotein IIb/IIIa (by Reopro, Integrilin or Aggrastat), and infusion of nitroglycerin all decrease PCF and CEM. Thus these parameters are not only useful in the identification of high risk patients, they can be used to monitor response to therapy.

BRIEF DESCRIPTION OF THE DRAWINGS

The foregoing and other objects, aspects and advantages will be better understood from the following detailed description of the preferred embodiments of the invention with reference to the drawings.

DETAILED DESCRIPTION OF THE PREFERRED EMBODIMENTS OF THE INVENTION

Figure 1:
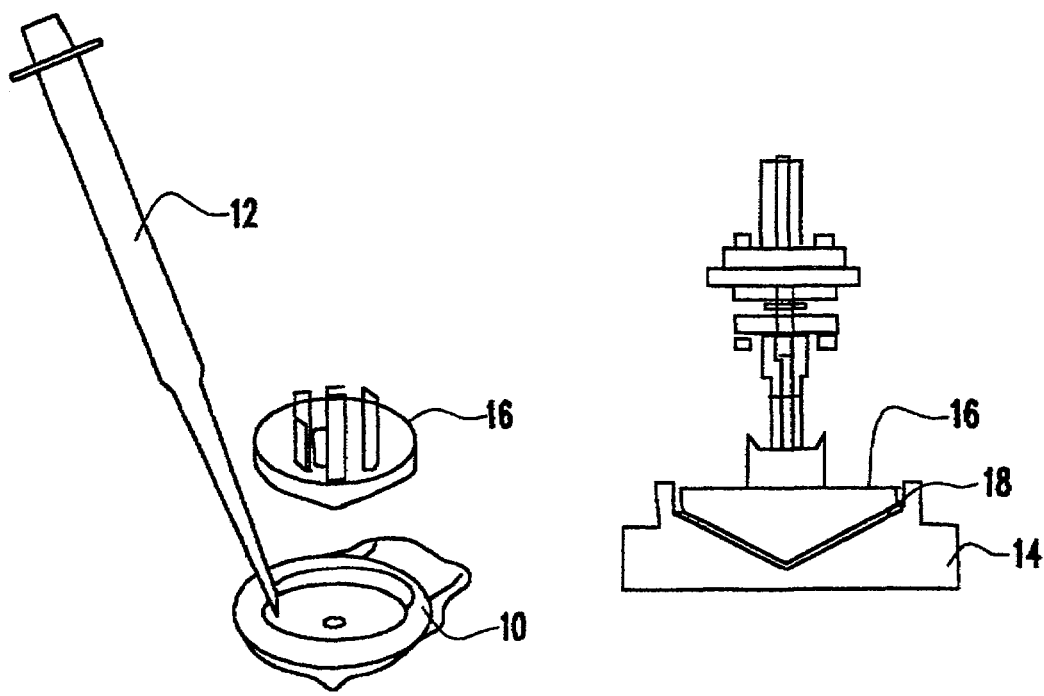
FIG. 1 is a schematic diagram of measurement system used to monitor platelet contractile force and clot elastic modulus during clot formation in whole blood. Anticoagulated whole blood is placed in a shallow conical cup and clot formation is initiated by the addition of clotting agent. Prior to clot formation a conical upper plate is lowered onto the upper surface of the sample, trapping the sample between parallel surfaces separated by a known distance. Platelets within the sample attempt to collapse the clot resulting in a downward force on the upper platelet. This downward force is continuously monitored and the elastic modulus of the forming clot is intermittently measured.
Figure 2:
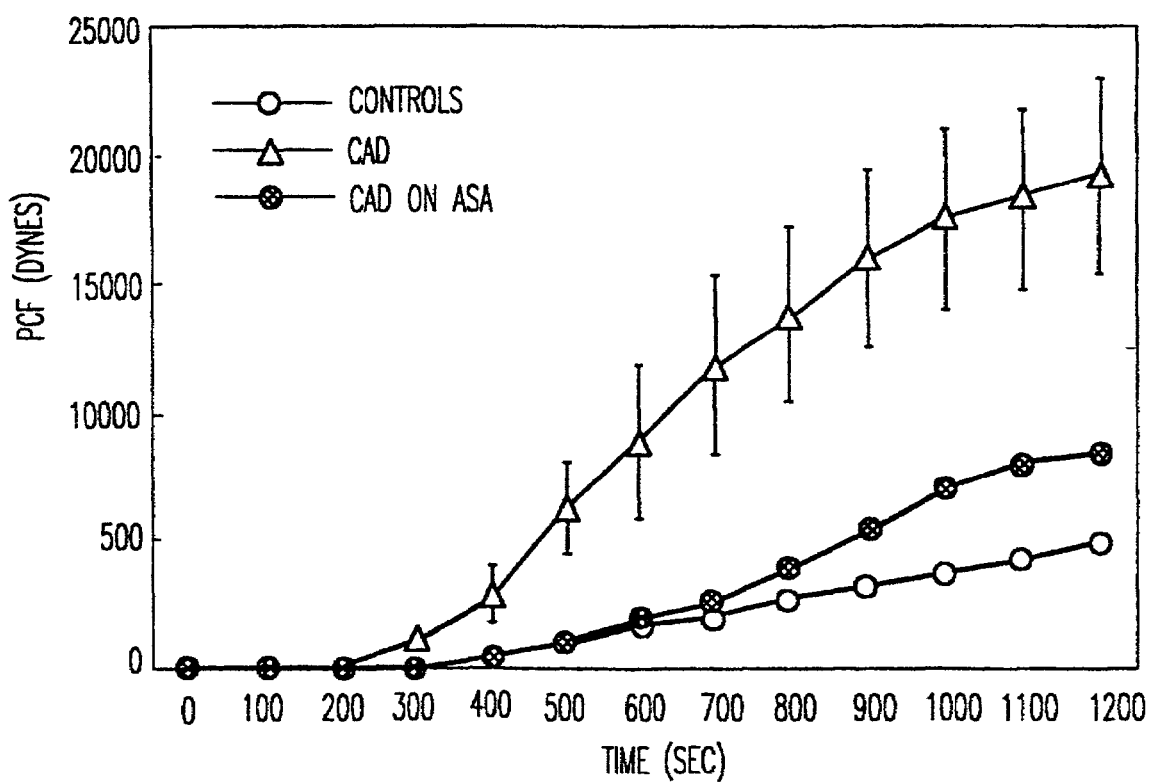
FIG. 2 is a graph which shows that preoperative platelet contractile force (PCF) is elevated in patients with documented coronary artery disease (CAD) who are undergoing coronary artery bypass grafting (CABG). The forces are higher in all such patients but are much higher in such patients who are not taking aspirin. Aspirin appears to decrease but does not normalize PCF values.
Figure 3:
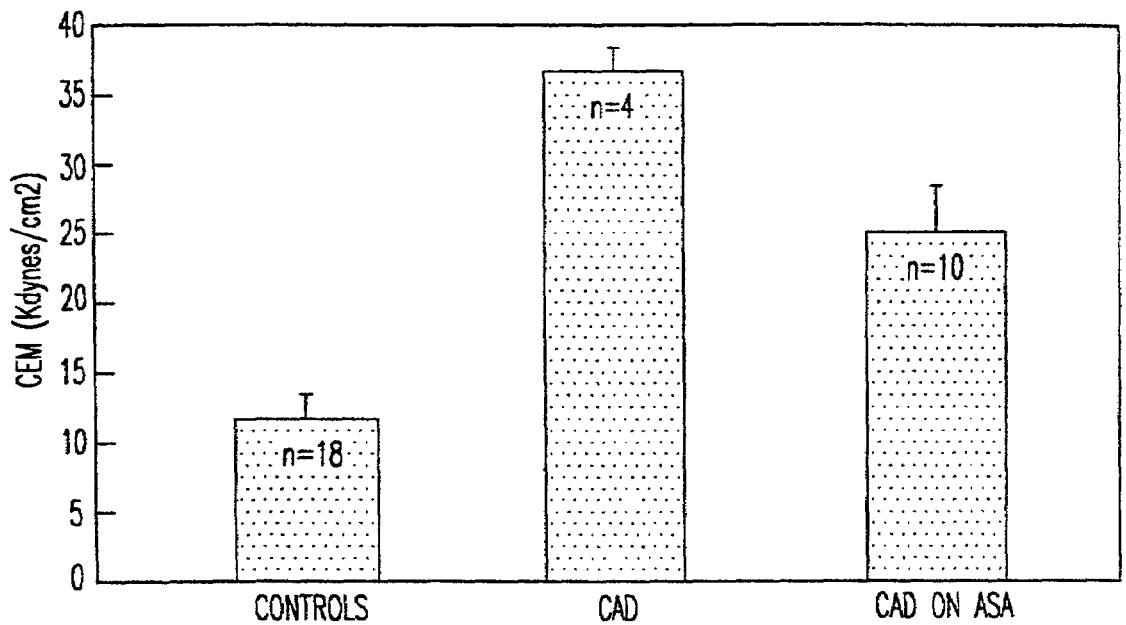
FIG. 3 is a bar graph which shows the effect of aspirin on whole blood clot elastic modulus (CEM) in patients with documented CAD who are undergoing CABG. CEM were measured at the time of maximal clot retraction. Values for patients with CAD taking or not taking aspirin were significantly elevated over those of asymptomatic control volunteers ($p<0.0002$).

The invention contemplates making PCF and/or CEM measurements on whole blood clots obtained from patient samples during clot formation, and then using these measurements as a screen to identify patient's at risk for an adverse vascular outcome. Application of this technique to clinical samples confirmed that clots with low PCF and/or CEM were less hemostatic and placed the patient at risk for bleeding in conditions such as primary fibrinolysis, Glanzmann thrombasthenia and coronary artery bypass procedures. PCF values less than 4 kilodynes after 720 seconds of clotting are abnormally low. Patients with severe thrombasthenia typically have PCF values below 2 kilodynes. CEM is affected by both fibrinogen concentration and platelet function. CEM values less than 14 kilodynes per $cm^2$ are indicative of deficient clot formation. In addition, application of this technique to clinical samples confirms that elevations of PCF and CEM are associated with arteriovascular disease and increased risk of arterial thrombosis. Specifically, patients with coronary artery disease, hypercholesterolemia, and diabetes mellitus have much higher PCF and CEM values than asymptomatic controls. In addition, patients who present to the emergency department with complaints of chest pain have significantly elevated forces and the degree of elevation increases with increasing clinical risk. PCF increases with age in males. However, while slightly higher in young females than in young males, PCF does not increase with age in females at least to the point of menopause. Elevated whole blood PCF and CEM values should help identify patients at increased risk of arterial thrombosis due to atherosclerosis and enhanced platelet function. These measurements should prove useful during the triage of chest pain patients in the emergency department as well as the screening of asymptomatic patients with positive family histories or other documented risk factors for atherosclerosis. Since most therapeutic measures used to acutely treat arterial thrombosis reduce PCF and/or CEM, these parameters can also have applications as monitors of clinical response.

Screening of asymptomatic individuals with PCF and CEM measurements could be useful in identifying patients who might benefit from more invasive and expensive testing. This can be accomplished by testing a small sample of venous blood. If the PCF value is greater than one standard deviation above the mean of normals, greater than 8.5 kilodynes and the patient has a positive family history or other risk factors (diabetes, cigarette smoking, hypercholesterolemia, etc.), then they should undergo additional testing. If the PCF is normal, 6.9±0.7 kilodynes, no additional testing is needed. If the PCF is above 7.6, testing at intervals to assess whether the force is increasing would be appropriate.

Methods

Patient Selection

All patients who present to the emergency department (ED) of the Medical College of Virginia/Virginia Commonwealth University (MCV) with symptoms suggestive of cardiac ischemia undergo prompt clinical evaluation which includes a history, physical exam and ECG. 99 patients presenting to ED with chest pain were recruited for this. When appropriate, blood samples, EKG and a brief history were performed by the ED nursing staff prior to the ED physician interview. Blood samples were obtained prior to the initiation of any therapeutic measures. Further management including early perfusion imaging with technetium-99m was based on the discretion of individual ED physician and a well established chest pain protocol[24]. Table 1 sets for the acute cardiac evaluation and therapy guide under the protocol.

TABLE 1

Acute Cardiac Evaluation and Therapy Guide

| Diagnosis | Treatment |
| --- | --- |
| Level 1 | |
| Acute Myocardial Infarction | t-PA or primary PTCA |
| ST elevation | admit CCU |
| Posterior MI | |
| LBBB with strong clinical Suspicion for AMI | |
| Level 2 | |
| Unstable Angina | Standard USA protocol |
| Ischemic ST-depression or | |
| Ischemic T-wave inversion | |
| Acute onset CHF | |
| Known CAD with typical symptoms | |
| Level 3 | |
| Probable Unstable Angina | Imaging with Technetium-99m |
| Non-ischemic ECG & | CCU fast-track |
| Typical CP > 30 minutes | If rest nuclear imaging positive |
| Atypical CP > 30 minutes with | admit as level 2 |
| Multiple risk factors | If negative-stress cardiolite-ASAP |
| Level 4 | |
| Possible Unstable Angina | Rest imaging with Technetium-99m |
| Nonischemic EKG & | |
| Brief typical chest pain or | If negative-home with f/u stress in am |
| Prolonged atypical CP or | |
| Cocaine CP | If positive-CCU admit-treat as level 2 |
| Level 5 | |
| Noncardiac CP with clean-cut diagnosis | As appropriate |

The hospital course for admitted patients was followed for pre-selected endpoints.

Forty-eight controls were also recruited and similar blood samples were obtained. Exclusion criteria for the control population included no current illness, no history of coronary artery disease or cerebrovascular accident, no recent ingestion of nonsteroidal inflammatory agents including aspirin. Samples for the individual tests were run soon after venipuncture. The institutional review board approved the study protocol.

Sample Handling

A single 15-ml blood sample obtained via an aseptic venipuncture prior to any therapeutic measure was placed into evacuated tubes containing 3.8% sodium citrate. Collagen-induced platelet aggregation, measurements of platelet contractile force (PCF) and elastic modulus (EM) were run in duplicates on whole blood.

Platelet Aggregation

Platelet aggregation was measured utilizing a Chrono-Log® whole blood lumi-aggregometer. 450 μL of citrated whole blood was mixed with 450 μL of saline and placed in an aggregometer cuvette equipped with a stirring bar. Platelet aggregation was induced by the addition of collagen (3 mg/ml, Chronolog, Havertown, Pa.) and the change in impedance was monitored for six minutes.

Measurement of Platelet Contractile Force and Clot Elastic Modulus/Clot Formation Human thrombin, greater than 90% alpha, was purchased as a lyophilized powder from Sigma Chemical Co. (St. Louis, Mo.). The material with a specific gravity of 3000 NIH units/ml was dissolved in water, diluted with 0.10 M NaCl to a final concentration of 225 units/ml, divided into 50 μL lots and frozen at 80° C. Thrombin was free of plasmin and plasminogen. Nanopure water was used in the preparations of all solutions. Clotting was initiated by adding thrombin (1 NIH unit/ml) and calcium chloride (10 mM) to 700 μL of whole blood. Force development was measured for 900 seconds.

The Hemodyne® RM-2 hemostasis analyzer (Hemodyne, Inc., Richmond, Va., USA) measures forces generated by platelets within a clot formed between two parallel cone-shaped plates (FIG. 1). The temperature of the sample is held constant via thermal control of the bottom cone, which serves as the sample cup. Before gelation, the upper cone is centered above the cup and lowered into the clotting solution. As the clot forms, it attaches to the inner walls of the cup and upper cone. The entire sample volume is contained between the upper and lower surfaces. Once clotting is complete, platelets within the network pull fibrin strands inward transmitting force through the network to the surfaces to which the clot is adherent. Force measurement is accomplished utilizing a displacement transducer coupled to the upper cone. As platelets contract, the transducer produces an electrical output proportional to the amount of force generated. Platelet contractile force is determined by measuring the amount of displacement ($\Delta V_2$) of the upper cone during the course of the reaction. In order to compensate for the changing rigidity of the fibrin network, a calibrated compressive force ($F_{applied}$) is periodically applied to the sample by means of an electromagnetic solenoid, and the resulting voltage signal ($\Delta V_1$), due to the displacement of the gel, is measured. PCF is then calculated as follows: $PCF = \Delta V_2 \times (F_{applied}/\Delta V_1)$ Clot Elastic Modulus (CEM) is obtained simultaneously with the PCF. The ratio of applied force (stress) to measured displacement (strain) is used to calculate the elastic modulus: CEM=stress/strain. Where stress equals the applied force ($F_{applied}$) divided by the area of application, and strain is the degree of shape change induced by the applied force. In the present case, the strain induced by $F_{applied}$ is measured as the change in gel thickness, which is the same as the change in the gap between the two cones. Strain is recorded as the ratio of the change in gap distance ($d_1$) to the original gap distance ($d_0$). Because the gel is a cylinder of radius ($r$) and length $d_0$, stress=$F_{applied}/pr^2$, strain=$d_1/d_0$ and CEM= $(F_{applied}/pr^2)/(d_1/d_0)$ The distance moved ($d_1$) is measured directly by the displacement transducer.

Sestamibi Imaging and Interpretation

Chest pain patients were injected with ~20 mCi sestamibi in the emergency department (not more than 6 hours after the last episode of chest pain) as per the chest pain protocol. Perfusion images were evaluated by an experienced nuclear medicine attending physician and all data were made available to the physicians treating the physician. For purposes of this study, images were classified as either positive or negative for acute myocardial infarction (MI) or ischemia. A positive study required a discrete perfusion defect with associated abnormalities in wall motion and thickening. Studies visually interpreted as normal, equivocal or consistent with cardiomyopathy were considered negative for acute coronary syndromes. Normal studies had normal perfusion and systolic function without regional wall motion or thickening abnormalities. Studies consistent with cardiomyopathy showed reduced systolic function on cinematic replay with either normal perfusion or perfusion defects without accompanying segmental wall motion abnormalities.

Endpoints

Patients who were admitted to the hospital were followed for specific endpoints. The primary endpoints were myocardial infarction, death, or urgent revascularization (coronary artery bypass graft surgery (CABG), or percutaneuous transluminal coronary angioplasty (PTCA) during the initial evaluation or within 5 days of admission.

Definitions

Myocardial infarction was defined as CK-MB mass$\geq$8.0 ng/dl with a relative index (CK-MB mass/total CK$\times$100)$\geq$ 4.0. For patients having both MI and revascularization, only MI was counted as an event. Anginal symptoms were considered typical if they were described as pressure, tightness, squeezing, burning, heaviness, crushing, or indigestion, or were similar to prior symptoms of angina.

Statistical Analysis

Results were presented as mean value ±SD. Comparisons were made using the Student's t-test and chi-square analysis for categoric and continuous variables. A p-value<0.05 was considered significant. The relative risk was calculated for various variable correlation coefficients.

Results

Baseline Demographics

The baseline demographics in the patients with chest pain and control patients are given in Table 2. The mean age was 52.8±13.9 (23–87) in the chest patients as compared to 37.7±10.1 (19–62) which was statistically significant. A significant difference in race and sex were also present. There were more blacks in the chest pain group and a preponderance of chest pain patients were male when compared to the control population. As expected, the chest pain patients had a greater number of traditional risk factors as compared to the control population.

TABLE 2

Baseline Demographics in Patients with Chest Pain and in Control Patients

|  | Chest Pain Patients | Control |
|---|---|---|
| Number | 99 | 46 |
| Age (years) | 52.8 ± 13.9(23–87) | 37.7 ± 10.1(19–62) |
| Gender |  |  |
| Male | 54(54.5%) | 23(47.9%) |
| Female | 45(45.5%) | 25(52.5%) |

TABLE 2-continued

Baseline Demographics in Patients with Chest Pain and in Control Patients

|  | Chest Pain Patients | Control |
|---|---|---|
| Race |  |  |
| Black | 71(71.7%) | 6(12.5%) |
| White | 28(28.3%) | 32(66.7%) |
| Asian |  | 10(20.8%) |
| Smoking Status |  |  |
| Current Smoker | 39(39.4%) | 3(6.5%) |
| H/O Diabetes Mellitus | 20(20.2%) | None |
| H/O Hypertension | 14(14.1%) | 2(4.4%) |
| H/O Hypercholesterolemia | 28(28.3%) | 1(2.2%) |
| Mean Platelet Count ($\times 10^3$) | 254 ± 76(149–541) | 257 ± 53(181–367) |
| Mean Hemoglobin (g/dl) | 13.2 ± 1.8(9.2–17) |  |
| Mean time to sample run (mts) | 149 ± 83.9 | 91.5 ± 68.3(10–345) |

Risk Stratification/Myocardial Infarction & Revascularization

Figure 4:
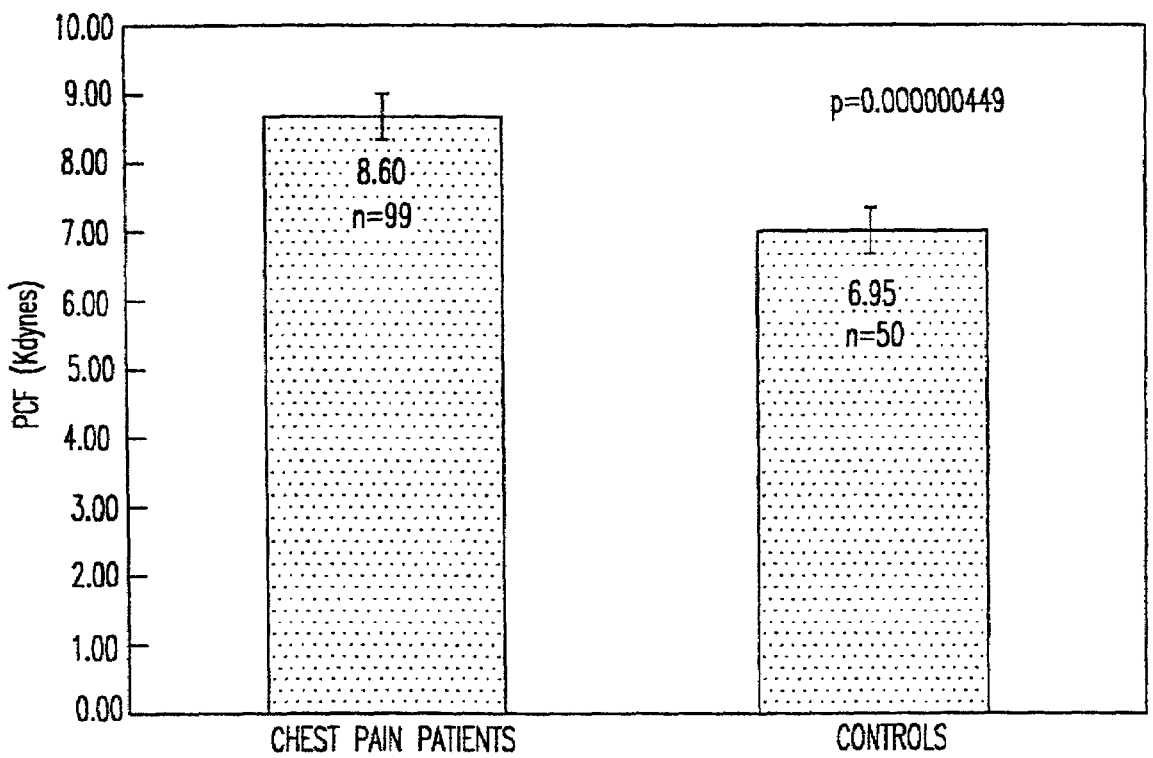
FIG. 4 is a bar graph which shows PCF is elevated in patients presenting in the emergency department with a complaint of chest pain. Samples for PCF and CEM determinations were obtained from 99 such patients soon after their arrival in the emergency room. The technician performing the assays did so without knowledge of the patient's clinical status. Upon presentation patient PCF values were significantly higher ($p=0.000000449$) than those seen in 50 asymptomatic volunteers.
Figure 5:
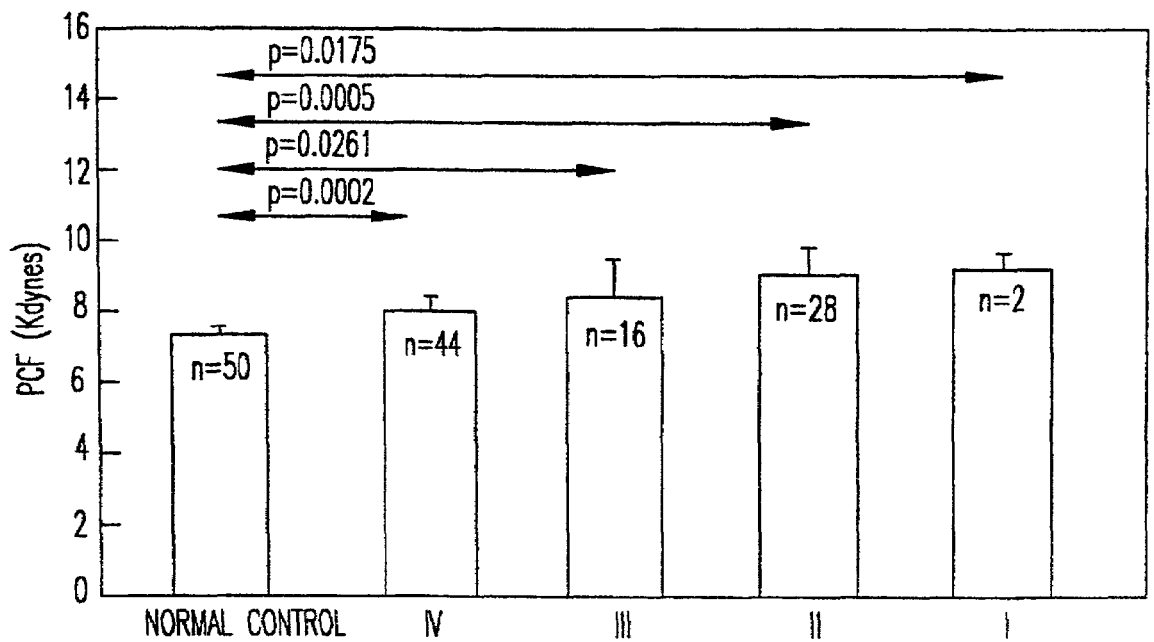
FIG. 5 is a bar graph which shows PCF values increase with the severity of the patient's clinical presentation. While all groups of patients had significantly elevated PCF values, those patients with electrocardiographic evidence of cardiac ischemia (levels II and I) had the highest PCF levels.
Figure 6:
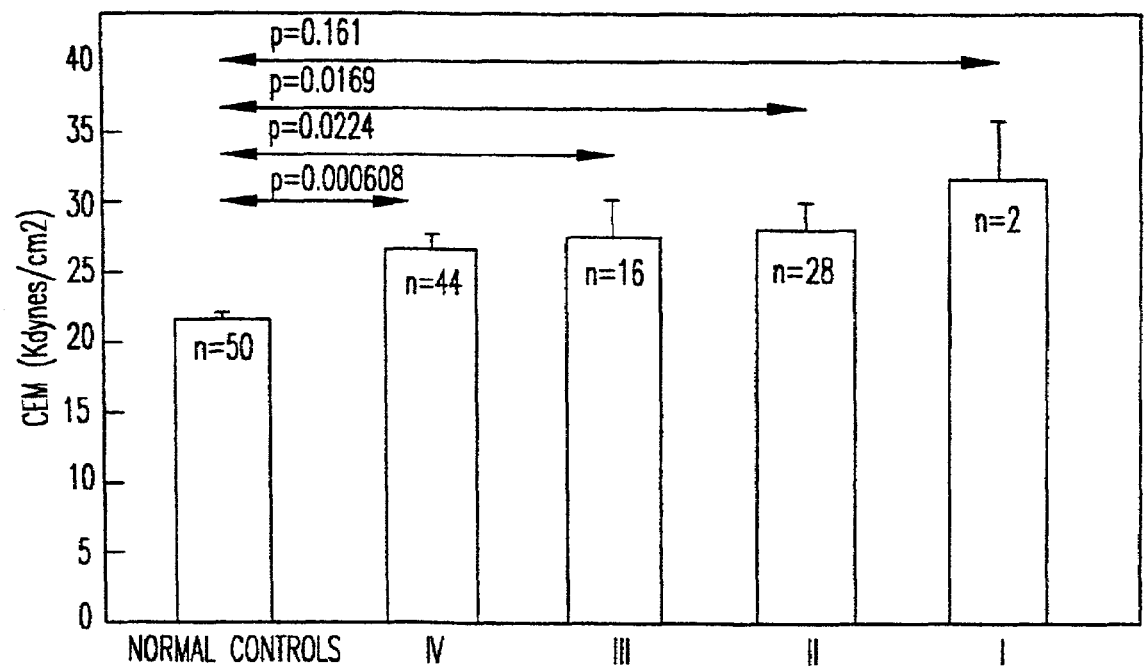
FIG. 6 is a bar graph which shows CEM is elevated in patients presenting in the emergency department with a complaint of chest pain. Upon presentation patient CEM values were significantly higher ($p=0.0000145$) than those seen in 50 asymptomatic volunteers.

All chest pain patients versus controls. PCF was significantly elevated (8.60±0.238 Kdynes) in patients presenting with chest pain as compared to controls (6.95±0.214 Kdynes)) (see FIG. 4). PCF was highest in patients with more critical chest pain protocol levels (I&II), but was significantly elevated at all levels (see FIG. 5). PCF for I & II level patients grouped together versus grouped III & IV levels approached but did not reach statistical significance (p=0.0735). CEM was also significantly elevated for all levels of chest pain patients compared to normals (FIG. 6).

Figure 7:
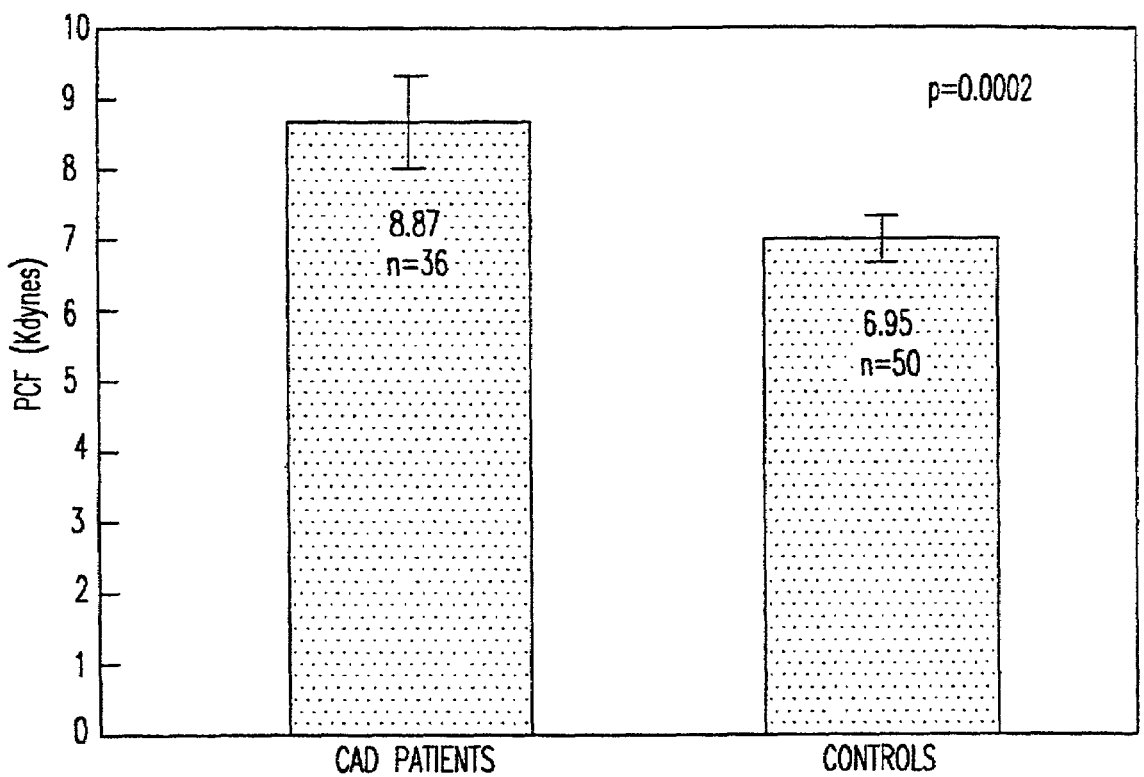
FIG. 7 is a bar graph which shows PCF was significantly elevated in chest pain patients who are subsequently documented to have CAD ($p=0.0002$).
Figure 8:
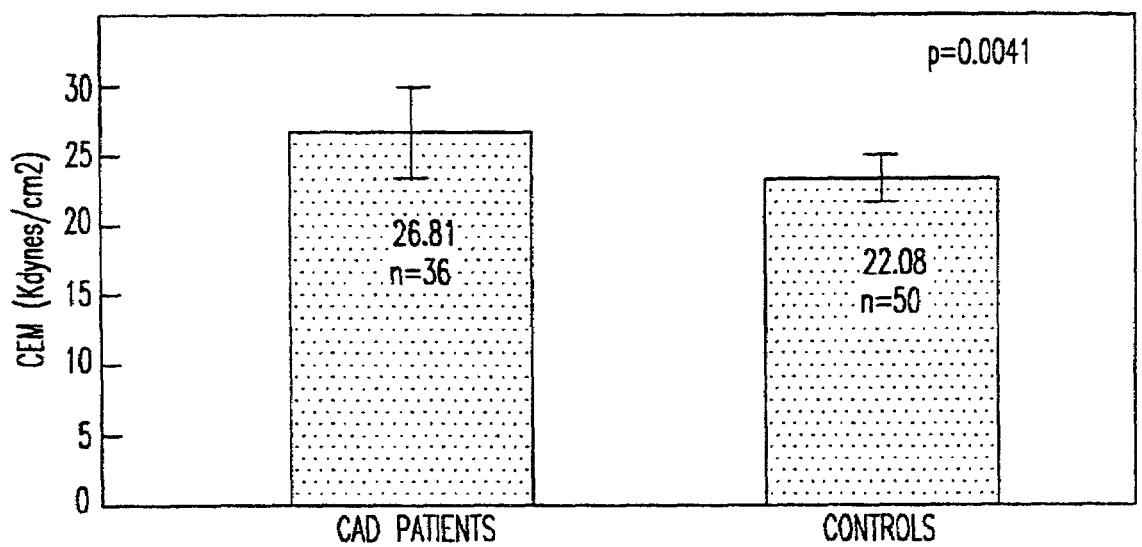
FIG. 8 is a bar graph which shows CEM was significantly elevated in chest pain patients who are subsequently documented to have CAD ($p=0.0041$).

Patients with CAD versus controls. Thirty-six of the 99 patients were documented to have coronary artery disease (CAD) by cardiac catheterization or the occurrence of an acute clinical event. PCF was significantly (p=0.0002) elevated in these patients (8.87±0.459 Kdynes) compared to controls (6.95±0.214 Kdynes) (see FIG. 7). CEM was significantly (p=0.0041) elevated in these patients (26.81±1.606 Kdynes/cm$^2$) compared to controls (22.08±0.588 Kdynes/cm$^2$) (see FIG. 8).

Figure 9:
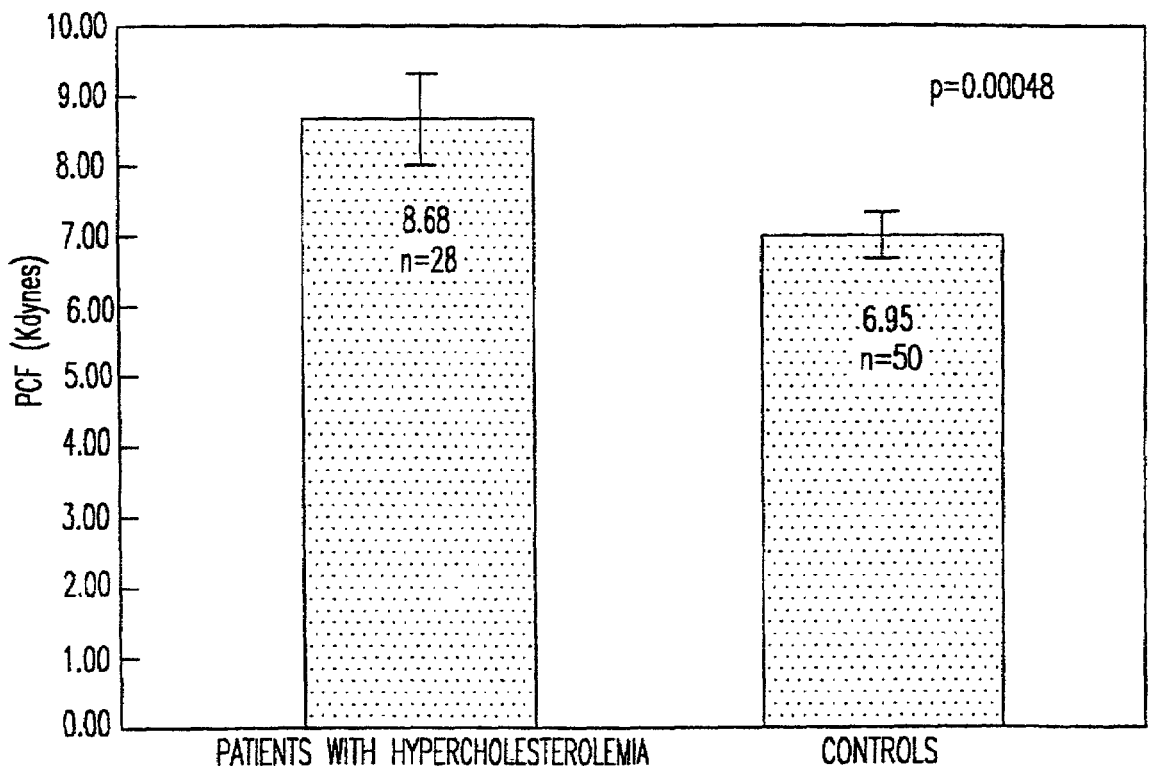
FIG. 9 is a bar graph which shows PCF is significantly elevated in patients with hypercholesterolemia ($p=0.00048$).
Figure 10:
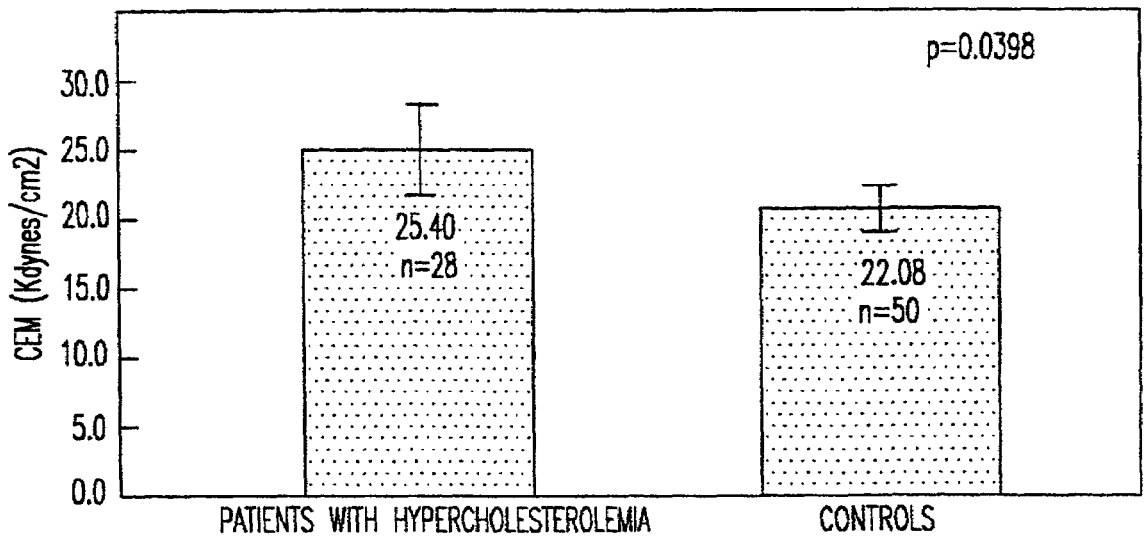
FIG. 10 is a bar graph which shows CEM is significantly elevated in patients with hypercholesterolemia ($p=0.0398$).

Patients with Hypercholesterolemia versus controls. Twenty-eight of the 99 patients were documented to have serum cholesterols greater than 220 mg/dL. PCF was significantly (p=0.00048) elevated in these patients (8.68±0.434 Kdynes) compared to controls (6.95±0.214 Kdynes) (see FIG. 9). CEM was significantly (p=0.0398) elevated in these patients (25.40±1.742 Kdynes/cm$^2$) compared to controls (22.08±0.588 Kdynes/cm$^2$) (see FIG. 10).

Figure 11:
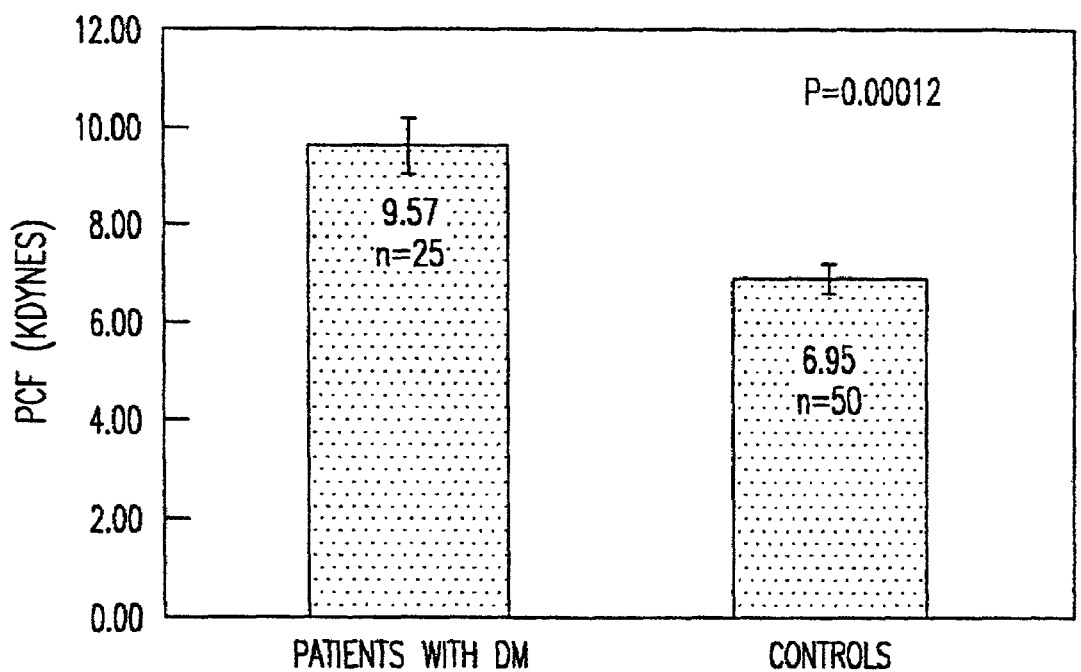
FIG. 11 is a bar graph which shows PCF is significantly elevated in patients with diabetes mellitus ($p=0.00012$).
Figure 12:
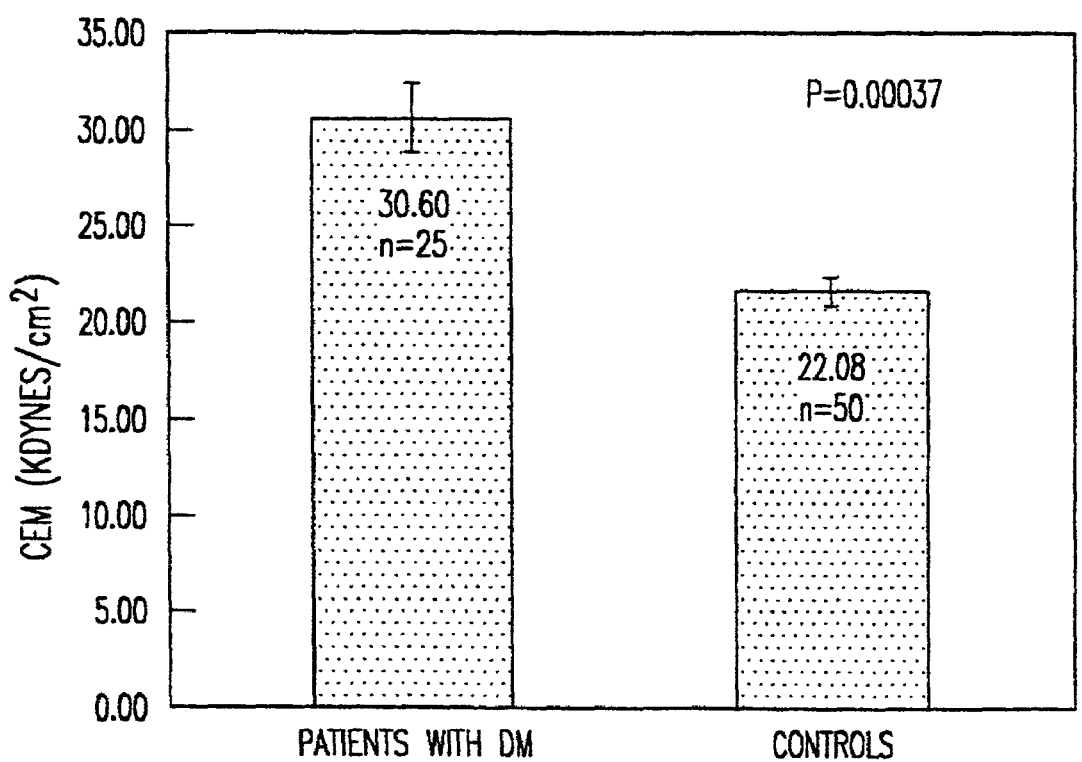
FIG. 12 is a bar graph which shows CEM is significantly elevated in patients with diabetes mellitus ($p=0.00037$).

Patients with Diabetes Mellitus versus controls. Twenty-five of the 99 patients were shown to have hemoglobin Alc levels greater than 7.0. PCF was significantly (p=0.00012) elevated in these patients (9.57±0.591 Kdynes) compared to controls (6.95±0.214 Kdynes) (see FIG. 11). CEM was significantly (p=0.00037) elevated in these patients (30.60±2.174 Kdynes/cm$^2$) compared to controls (22.08±0.588 Kdynes/cm$^2$) (see FIG. 12).

Patients with Positive versus Negative Sestamibi. Sixty-four of the 99 patients underwent sestamibi scanning. Fifteen of these sixty-four patients had a positive scan. PCF tended to be higher in patients with positive (9.4±0.8 Kdynes) versus negative (8.2±0.3 Kdynes) although the difference did not reach statistical significance (p=0.08). Similarly, CEM tended to be higher in patients with positive (29.9±2.6 Kdynes/cm$^2$) versus negative (25.2±1.1 Kdynes/cm$^2$) although the difference did not reach statistical significance (p=0.07).

Figure 13:
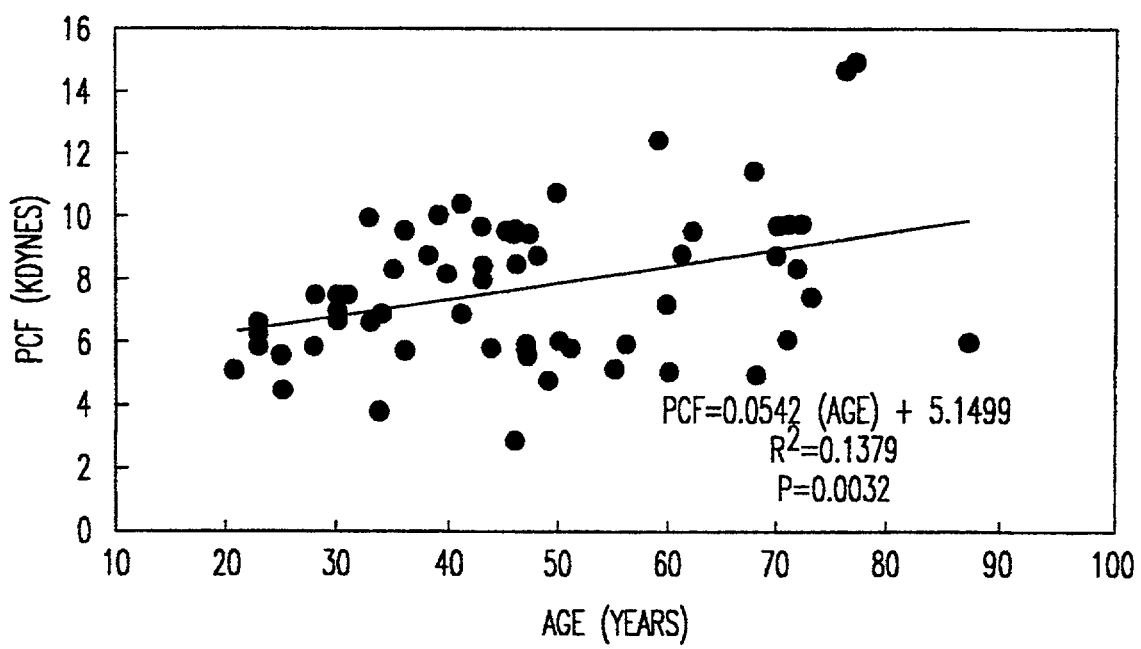
FIG. 13 is a line graph that shows that in the chest pain study, PCF increased with age in both patient and asymptomatic males. The correlation was statistically significant ($p=0.0032$).
Figure 14:
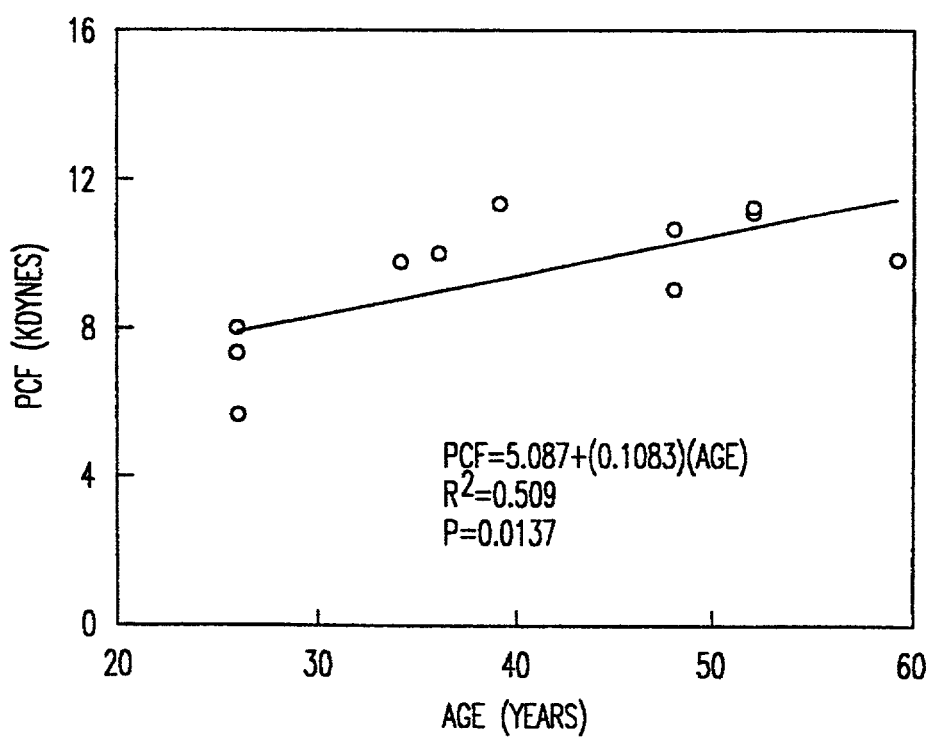
FIG. 14 is a line graph that shows PCF increased with age in a separate study of apparently normal Italian males ($p=0.0137$).
Figure 15:
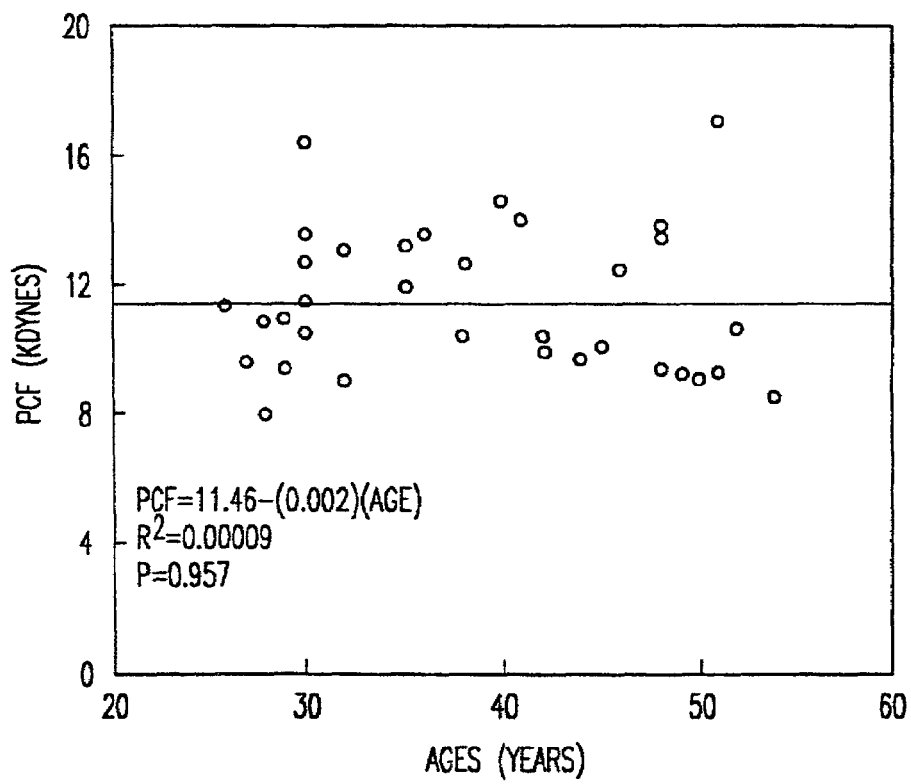
FIG. 15 is a line graph that shows that in the Italian study, PCF did not change with age in females under the age of 60.

Patients with positive clinical endpoints. Seven patients (7.07%) were documented to have suffered a myocardial infarction (MI). An additional five patients (5.05%) underwent revascularization. Total group of MI and revascularization patients was twelve of ninety-nine (12.12%). PCF was significantly (p<0.05) elevated (8.2±0.7 Kdynes) in the positive endpoint group compared to normals (6.9±0.2 Kdynes). Similarly, CEM was significantly (p<0.05) elevated (24.9±1.9 Kdynes/cm$^2$) in the positive endpoint group compared to normals (21.7±0.6 Kdynes/cm$^2$). Effect of Age. PCF increased with age when all males (patients and controls) were considered as one group (FIG. 13). This result was confirmed in a smaller Italian study of asymptomatic males (FIG. 14). PCF did not increase with age in American or Italian (FIG. 15) females. It is to be noted that this result has only been confirmed in females below the age of fifty-five.

Figure 16:
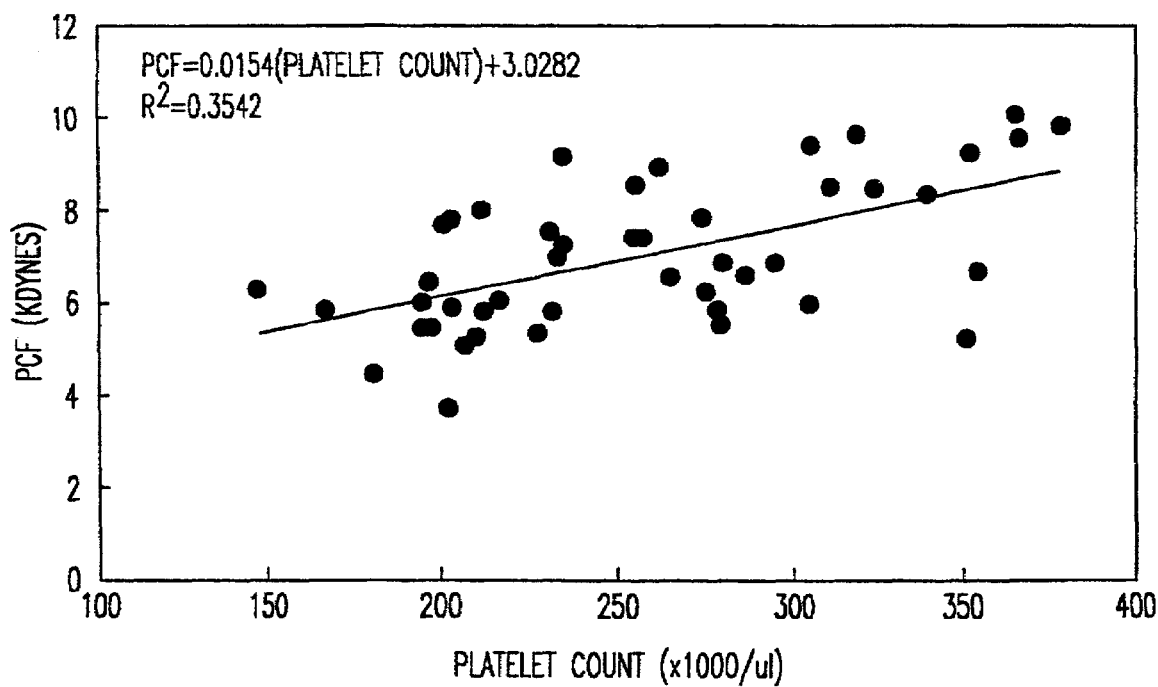
FIG. 16 is a line graph that shows that PCF increases with platelet count in all populations studied. The slope of the regression line allows calculation of an average force per platelet number for varying populations. Patients with known arteriovascular disease have higher force per platelet values than asymptomatic age matched controls (see table 3).

Platelet Force Per Platelet (FPP). PCF is dependent upon and increases with increasing platelet concentration (FIG. 16). However, the increased PCF values in chest pain patients were not due to elevated platelet counts (Table 2). Instead, the slope of the force versus platelet concentration plot (FIG. 16) was increased in similar plots for CAD and DM patients. Such plots allows the calculation of a new parameter—force per platelet (FPP). Table 3 shows FPP was highly significantly elevated in CAD and DM patients relative to asymptomatic controls.

TABLE 3

Mean Platelet Contractile Force Per Platelet Values for Various Test Groups

| Group | PCF/Platelet (Dynes × 10$^{-5}$/platelet) | p-value |
|---|---|---|
| Controls | 3.97 |  |
| Coronary Artery Disease | 5.309 | 0.000217 |
| Diabetes Mellitus | 6.19 | 0.000743 |

Figure 17:
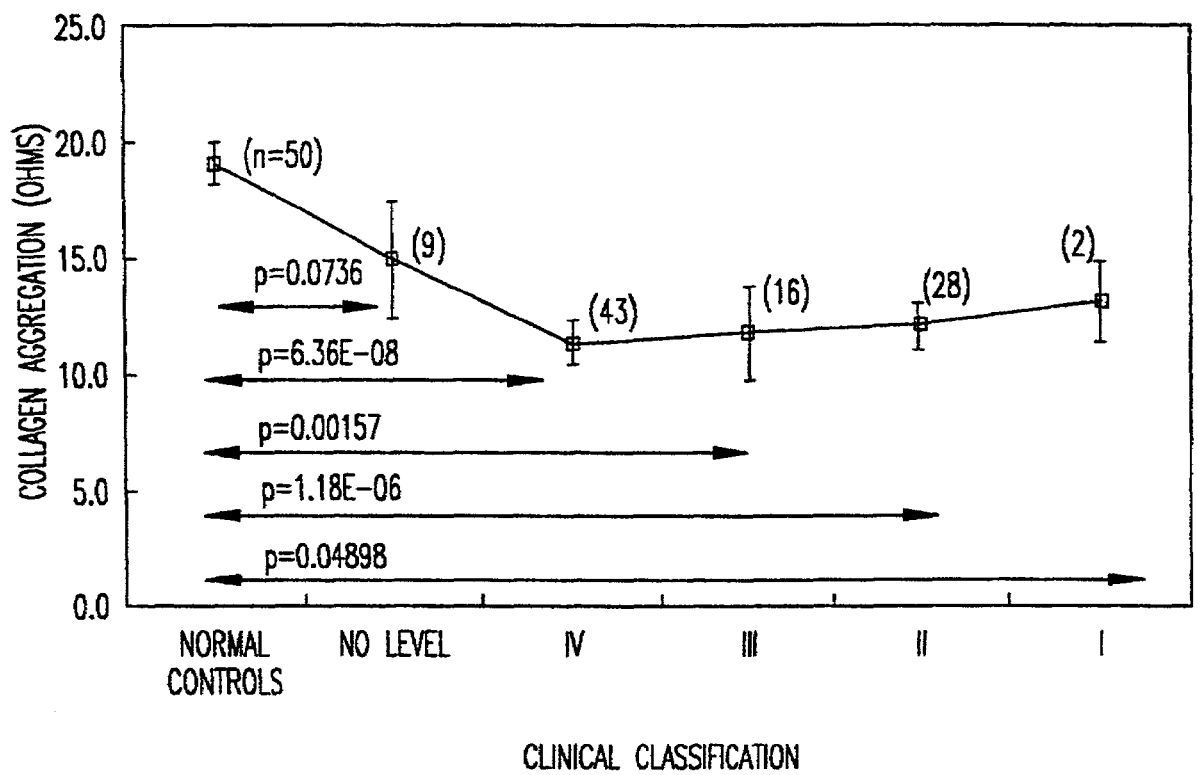
FIG. 17 is a line graph that shows that collagen-induced whole blood platelet aggregation was depressed in patients presenting in the emergency department with a complaint of chest pain. Samples for aggregation were obtained from 99 such patients soon after their arrival in the emergency room. The technician performing the assays did so without knowledge of the patient's clinical status. Upon presentation patient aggregation values were significantly lower (p=0.000000449) than those seen in 50 asymptomatic volunteers. While all groups of patients had significantly decreased aggregation, aggregation did not vary significantly between the varying risk levels.

Platelet Aggregation in Chest Pain Patients versus controls. Collagen induced whole blood platelet aggregation was significantly reduced in patients presenting the emergency department with chest pain (FIG. 17). However, the degree of suppression did not correlate with clinical risk levels.

Table 4 contains a complete odds ratio analysis for the chest pain study.

TABLE 4

Odds Ratio Analysis for PCF and EM versus known risk factors for atherosclerosis and coronary artery disease

|  | PCF | | EM | |
|---|---|---|---|---|
|  | OR(CI) | p value | OR(CI) | p value |
| CAD | 2.0(0.5–7.4) | ns | 1.3(0.4–4.6) | ns |
| DM | 2.7(1.7–7.3) | 0.06 | 2.7(1.7–7.3) | 0.06 |
| Hypercholesterol | 1.6(0.6–4.4) | 0.31 | 0.7(0.3–2.2) | 0.7 |
| Male | 0.6(0.2–1.6) | 0.4 | 1.1(0.4–2.6) | ns |
| Tobacco | 1.1(0.4–2.9) | 0.1 | 0.8(0.3–2.1) | 0.8 |
| Age ≥ 60 | 1.6(0.6–4.1) | 0.5 | 1.4(0.6–3.7) | ns |
| LVEF ≤ 45% | 0.6(0.12–3.3) | 0.7 | 3.9(1.2–12.2) | <0.05 |
| Black Race | 2.4(0.7–7.8) | 0.2 | 1.8(0.6–5.5) | 0.3 |

REFERENCES

1. Willerson J T, Cohen. Cardiovascular Medicine.
2. Fitzerald D J, Louis R, Catella F, Fitzerald G A. Platelet activation in unstable coronary disease. *NEJM* 315:983–9, 1986.
3. Willerson J T et al. Conversion from chronic to acute coronary artery disease: Speculation regarding mechanisms. *American Journal of Cardiology* 54: 1349–54, 1981.
4. Buja M L, Willerson J T: Clinicopathologic correlates of acute ischemic heart diseasesyndromes. *American Journal of Cardiology* 47:343–356, 1981.
5. Willerson J T et al. Specific platelet mediators and unstable coronary artery lesions. Experimental evidence and potential clinical implications. *Circulation* 80,1:198–205, 1989.
6. Lee, T H, Rouan G W, Weisberg M C et al. Clinical characteristics and natural history of patients with acute myocardial infarction sent home from the emergency room. *Ann Emerg Med* 16: 1145–50, 1987.
7. McCarthy B D, Behansky J R, D'Agostino R B, Selker H P. Missed diagnosis of acute myocardial infarction in the emergency department: results from a multicenter study. *Ann Emerg Med* 22: 579–82, 1993
8. Kontos M C, Jesse R L, Schmidt K I, Omato J P, Tatum J I. Value of acute rest sestamibi perfusion imaging for evaluation of patients admitted to the emergency department with chest pain. *JACC* 30: 976–82.
9. Varetto T, Cantalupi, Altieri A, Orlandi C. Emergency room technetium-99m sestamibi imaging to rule out acute myocardial ischemic events in patients with nondiagnostic electrocardiograms. *JACC* 22: 1804–1808, 1993.
10. Hilton T C, Thompson R C, Williams H J, Saylors R, Fulmer H. Stowers S A. Technetium-99m sestamibi myocardial perfusion imaging in the emergency room evaluation of chest pain. *JACC* 23 1016–22, 1994
11. Ohman E M, Armstrong P W, Christenson R H et al. (GUSTO IIA Investigators) Cardiac troponin T levels for risk stratification acute myocardial ischemia. *NEJM* 335: 133–41, 1996.
12. Trip M D, Volkert M C, Van Capelle F J L, Vreeken J. Platelet hyperactivity and prognosis in survivors of myocadial infarcion. *NEJM* 322: 1549–54, 1990.
13. Ikeda H, Nakayama H, Oda T, Kuwano K, Muraishi A, Sugi K, Koga Y, Toshima H. Soluble form of P-selectin in patients with acute mycardial infarcion. *Coronary Artery Disease June;* 5: 515–8, 1994.
14. Shyu K G, Chang H, Lin C C, Kuan P. Circulating intercellular adhesion molecule-1 and E-selectin in patients with acute coronary syndrome. *Chest* 109:1627–30, 1996.
15. Carr M E, Zekert S L. Measurement of Platelet Mediated-Force Development during Plasma Clot Formation. *Am J Med Sci* 302:13–18, 1991.
16. Carr M E: Measurement of platelet force: the Hemodyne® hemostasis analyzer. *Clin Lab Management Rev* 9:312–319, 1995.
17. Carr M E, Zekert S L. Abnormal clot retraction, altered fibrin structure, and normal platelet function in multiple myeloma. *Am J Physiol (Heart Circ. Physiol.* 35) 266: H1195–H1201, 1994.
18. Carr M E, Zekert S L. Force monitoring of clot retraction during DDAVP therapy for the qualitative platelet disorder of uraemia: Report of a case. *Blood Coqgulation and Fibrinolysis* 2:303–308, 1991.
19. Greilich P E, Carr M E, Carr S L, Chang A S. Reductions in Platelet Force Development by Cardiopulmonary Bypass Are Associated with Hemorrhage. *Anesthes Analges* 80:459–465, 1995.
20. Alving B M, Reid T J, Fratantoni J C, Finlayson J S. Frozen platelets and platelet substitutes in transfusion medicine. *Transfusion* 37:866–876, 1997.
21. Reid T, Snider R, Hartman K, Greilich P E, Carr M E, Alving B M. A Method for the quantitative assessment of platelet-induced clot retraction and clot strength in fresh and stored platelets. *Vox Sang* 75:270–277, 1998.
22. Carr M E, Carr S L, Hantgan R R, Braaten J: Glycoprotein IIb/IIIa Blockade Inhibits Platelet Mediated Force Development and Reduces Gel Elastic Modulus. *Thromb Haemostas* 73:499–505, 1995 Greilich P E, Carr M E, Carr S L, Chang A S: Reductions in Platelet Force
23. Greilich P E, Carr M E, Zekert S L, Dent R M: Quantitative Assessment of Platelet Function and Clot Structure in Patients with Severe Coronary Artery Disease. *Am J Med Sci* 307:15–20, 1994.
24. Tatum J L, Jesse R L, Kontos M C, et al. Comprehensive strategy for the evaluation and triage of the chest pain patient. *Ann Emerg Med* 29:116–23, 1997.

While the invention has been described in terms of its preferred embodiments, those skilled in the art will recognize that the invention can be practiced with modification within the spirit and scope of the appended claim.

We claim:

1. A method of monitoring treatment or therapy of a patient suffering from unstable angina or myocardial infarction, comprising the steps of:

obtaining a baseline measurement on a blood sample taken from said patient selected from the group consisting of platelet contractile force and clot elastic modulus;

providing said patient with treatment or therapy;

obtaining a measurement on a blood sample taken after said step of providing, said measurement being selected from the group consisting of platelet contractile force and clot elastic modulus; and comparing said measurement and said baseline measurement, wherein progress of said treatment or therapy is indicated by a decline in said measurement relative to said baseline measurement.

2. The method of claim 1 wherein said measurement and said baseline measurement both provide platelet contractile force values.

3. The method of claim 1 wherein said measurement and said baseline measurement both provide clot elastic modulus values.

4. The method of claim 1, wherein the patient suffers from unstable angina.

5. The method of claim 1, wherein the patient suffers from myocardial infarction.

6. The method of claim 1, wherein the measurements are a force per platelet (FPP) parameter.

* * * * *